(12) United States Patent
LeFrancois et al.

(10) Patent No.: US 11,806,119 B2
(45) Date of Patent: Nov. 7, 2023

(54) ELECTRONIC DEVICE WITH OPTICAL HEART RATE MONITOR

(71) Applicant: Garmin Switzerland GmbH, Schaffhausen (CH)

(72) Inventors: Simon LeFrancois, Cochrane (CA); Paul R. MacDonald, Calgary (CA); Kristin A. Stevens, Calgary (CA)

(73) Assignee: Garmin Switzerland GmbH

( * ) Notice: Subject to any disclaimer, the term of this patent is extended or adjusted under 35 U.S.C. 154(b) by 557 days.

(21) Appl. No.: 16/820,044

(22) Filed: Mar. 16, 2020

(65) Prior Publication Data

US 2020/0297226 A1    Sep. 24, 2020

Related U.S. Application Data

(60) Provisional application No. 62/819,992, filed on Mar. 18, 2019.

(51) Int. Cl.
*A61B 5/024* (2006.01)
*A61B 5/00* (2006.01)
*A61B 5/1455* (2006.01)

(52) U.S. Cl.
CPC ...... *A61B 5/02427* (2013.01); *A61B 5/02433* (2013.01); *A61B 5/02438* (2013.01);
(Continued)

(58) Field of Classification Search
CPC . A61B 5/02427; A61B 5/02438; A61B 5/681; A61B 5/02433; A61B 5/14552; A61B 2562/0238; A61B 2562/046
See application file for complete search history.

(56) References Cited

U.S. PATENT DOCUMENTS 5,431,170 A    7/1995    Mathews
5,524,617 A    6/1996    Mannheimer
(Continued)

FOREIGN PATENT DOCUMENTS

EP    3111834 A1    1/2017
WO    2015116891 A1    8/2015
WO    2017027551 A1    2/2017

OTHER PUBLICATIONS

Lee et al., Bidirectional Recurrent Auto-Encoder for Photoplethysmogram Denoising, Publication Date: Dec. 5, 2018, IEEE Journal of Biomedical and Health informatics, 2018, pp. (Year: 2018).*

(Continued)

*Primary Examiner* — Toan M Le
(74) *Attorney, Agent, or Firm* — Samuel M. Korte; Max M. Ali

(57) ABSTRACT

An electronic fitness device includes a housing, a first optical transmitter array, a first optical receiver, and a second optical receiver. The first optical transmitter array is positioned at a first location on a bottom wall and may output a plurality of optical signals that pass through a user's skin. The first optical receiver is positioned at a second location and may receive the optical signals from the first optical transmitter array such that the optical signals travel along a first signal path and a first distance. The second optical receiver is positioned at a third location and may receive the optical signals from the first optical transmitter array such that the optical signals travel along a second signal path and a second distance, wherein the second signal path is roughly orthogonal to the first signal path and the second distance is different from the first distance.

20 Claims, 9 Drawing Sheets

(52) U.S. Cl.
CPC .......... *A61B 5/681* (2013.01); *A61B 5/14552* (2013.01); *A61B 2562/0238* (2013.01); *A61B 2562/046* (2013.01)

(56) References Cited

U.S. PATENT DOCUMENTS

| | | | |
|---|---|---|---|
| 5,632,272 | A | 5/1997 | Diab et al. |
| 9,292,008 | B1 | 3/2016 | Ahamed et al. |
| 10,215,698 | B2 | 2/2019 | Han et al. |
| 10,912,469 | B2 | 2/2021 | MacDonald et al. |
| 2003/0109775 | A1 | 6/2003 | O'Neil et al. |
| 2011/0060200 | A1 | 3/2011 | Bernreuter |
| 2012/0209095 | A1 | 8/2012 | Huiku |
| 2013/0030267 | A1 | 1/2013 | Lisogurski et al. |
| 2014/0213863 | A1 | 7/2014 | Loseu et al. |
| 2015/0065889 | A1 | 3/2015 | Gandelman et al. |
| 2015/0313549 | A1 | 11/2015 | Lee et al. |
| 2016/0287107 | A1 | 10/2016 | Szabados et al. |
| 2016/0296174 | A1 | 10/2016 | Isikman et al. |
| 2017/0020399 | A1* | 1/2017 | Shemesh ............ A61B 5/02416 |
| 2018/0317785 | A1 | 11/2018 | MacDonald et al. |
| 2018/0317786 | A1 | 11/2018 | Kulach et al. |
| 2018/0317852 | A1 | 11/2018 | MacDonald et al. |

OTHER PUBLICATIONS

Abstract of Lee et al., Publication Date: Dec. 5, 2018, 1 pp. (Year: 2018).*

Konijnenburg et al., A Battery-Powered Efficient Multi-Sensor Acquisition System with Simultaneous ECG, BIO-Z, GSR, and PPG, 2016 IEEE International Solid-State Circuits Conference, ISSCC 2016/ Session 28/ Biological Sensors for Point of Care/ 28.4, 3 pp. (Year: 2016).*

Printout from https://www.apple.com/newsroom/2018/09/redesigned-apple-watch-series-4-revolutionizes-communication-fitness-and-health/ published prior to Mar. 16, 2020.

Casson et al., Gyroscope vs. accelerometer measurements of motion from wrist PPG, during physical exercise, School of Electrical and Electronic Engineering, The University of Manchester, Manchester, UK, ICT Express 2, 2016, p. 175-179.

International Search Report and Written opinion from PCT/EP2018/061445 dated Aug. 16, 2018.

International Search Report and Written Opinion from PCT/EP2018/061446 dated Aug. 16, 2018.

International Search Report and Written Opinion from PCT/EP2019/061444 dated Aug. 16, 2018.

Nitzan et al., Pulse oximetry: fundamentals and technology update, Dove Press journal, Medical Devices: Evidence and Research Jul. 8, 2014.

Nogawa et al., Development of an optical arterial hematocrit measurement method: pulse hematometry. Engineering in Medicine and Biology 27th Annual Conference, Sep. 1-4, 2005.

Printout from https://www.pcmag.com/reviews/apple-watch-series-4 published prior to Mar. 16, 2020.

U.S. Appl. No. 15/969,553, Kulach, filed May 2, 2018.

U.S. Appl. No. 15/969,574, MacDonald, filed May 2, 2018.

Wieben, O., Light Absorbance in Pulse Oximetry, published prior to Jan. 3, 2018.

Yadhuraj et al., Motion Artifact Reduction in Photoplethysmographic Signals: A Review, International Journal of Innovative Research & Development, Mar. 2013, vol. 2, Issue 3, p. 626-640.

* cited by examiner

ELECTRONIC DEVICE WITH OPTICAL HEART RATE MONITOR

RELATED APPLICATIONS

The present patent application claims priority benefit under 35 U.S.C. § 119(e) of U.S. Provisional Patent Application Ser. No. 62/819,992, filed Mar. 18, 2019, and titled "Improved Optical Cardiac Monitor," which is hereby incorporated by reference in its entirety.

BACKGROUND

An electronic fitness device may provide optical cardiac monitoring of a user of the device. The user may wear the electronic device such that a housing of the electronic device is located in contact with the skin of the user—typically being worn on the user's wrist. The cardiac monitoring may include physiological metrics and information such as a user's heart rate and pulse oximetry. The electronic fitness device may include optical devices, such as an optical transmitter, which emits an optical signal into the user's skin, and an optical receiver, which receives transmissions or reflections of the optical signal from the skin and generates a photoplethysmogram (PPG) signal corresponding to the intensity of the received optical signal. The electronic fitness device processes the PPG signal to determine the user's heart rate and pulse oximetry. Occasionally, while the user is active or exercising, the electronic fitness device may move out of a normal position and become tilted on the user's wrist. In this situation, the optical transmitter and/or the optical receiver may become separated from the user's skin—leading to a lower optical signal level and a reduction in a signal to noise ratio of the PPG signal. Under these circumstances, the electronic fitness device may not be able to accurately determine the user's heart rate and pulse oximetry.

SUMMARY

Embodiments of the present technology provide an electronic fitness device with more robust operation that is capable of accurately determining a user's heart rate and pulse oximetry when the device becomes tilted on the user's wrist. The electronic fitness device broadly comprises a housing, a first optical transmitter array, a first optical receiver, and a second optical receiver. The housing includes a bottom wall configured to contact a user's wrist. The first optical transmitter array is positioned at a first location on the bottom wall and is operable to output a plurality of optical signals that pass through a user's skin, with each optical signal having a unique wavelength. The first optical receiver is positioned at a second location on the bottom wall and is operable to receive the optical signals from the first optical transmitter array such that the optical signals travel along a first signal path and a first distance from the first optical transmitter array to the first optical receiver. The second optical receiver is positioned at a third location on the bottom wall and is operable to receive the optical signals from the first optical transmitter array such that the optical signals travel along a second signal path and a second distance from the first optical transmitter array to the second optical receiver, wherein the second signal path is roughly orthogonal to the first signal path and the second distance is different from the first distance.

Another embodiment of the present technology provides an electronic fitness device comprising a housing, a first optical transmitter array, a second optical transmitter, a first optical receiver, a second optical receiver, a third optical receiver, and a fourth optical receiver. The housing includes a bottom wall configured to contact a user's wrist. The first optical transmitter array is positioned at a first location on the bottom wall and includes a first optical transmitter, a second optical transmitter, and a third optical transmitter, with each optical transmitter operable to output a first optical signal that passes through a user's skin. Each first optical signal has a unique wavelength. The second optical transmitter array is positioned at a second location on the bottom wall and including a first optical transmitter, a second optical transmitter, and a third optical transmitter, with each optical transmitter operable to output a second optical signal that passes through a user's skin. Each second optical signal has a wavelength equal to a wavelength of a corresponding first optical signal of the first optical transmitter array. The first optical receiver is spaced apart from the third optical receiver with the first optical transmitter array and the second optical transmitter array positioned therebetween. The second optical receiver is spaced apart from the fourth optical receiver with the first optical transmitter array and the second optical transmitter array positioned therebetween. Each optical receiver is operable to receive the first optical signals and the second optical signals. The first optical signals travel along a different signal path from the first optical transmitter array to each of the optical receivers, and the second optical signals travel along a different signal path from the second optical transmitter array to each of the optical receivers.

Another embodiment of the present technology provides an electronic fitness device comprising a housing, a memory element, a first optical transmitter array, a second optical transmitter, a first optical receiver, a second optical receiver, a third optical receiver, and a fourth optical receiver. The housing includes a bottom wall configured to contact a user's wrist. The memory element is configured to store a signal to noise ratio threshold. The first optical transmitter array is positioned at a first location on the bottom wall and is operable to output a plurality of first optical signals that pass through a user's skin. Each first optical signal has a unique wavelength. The second optical transmitter array is positioned at a second location on the bottom wall and is operable to output a plurality of second optical signals that pass through the user's skin. Each second optical signal has a wavelength equal to a wavelength of a corresponding first optical signal. Each optical receiver is positioned proximate to the first optical transmitter array and the second optical transmitter array. Each optical receiver is operable to receive the first optical signals and the second optical signals, and is operable to generate a first electronic signal corresponding to the first optical signals and a second electronic signal corresponding to the second optical signals. The processing element is coupled with the memory element and each of the optical receivers. The processing element is configured to: receive the first electronic signal and the second electronic signal from each of the optical receivers, determine a signal to noise ratio of each of the first electronic signals and the second electronic signals, and process the first electronic signals and the second electronic signals if the signal to noise ratio of the first electronic signals and the second electronic signals is above the signal to noise threshold.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present technology will be apparent from the following detailed description of the embodiments and the accompanying drawing figures.

BRIEF DESCRIPTION OF THE DRAWING FIGURES

Embodiments of the present technology are described in detail below with reference to the attached drawing figures, wherein.

Figure 1:
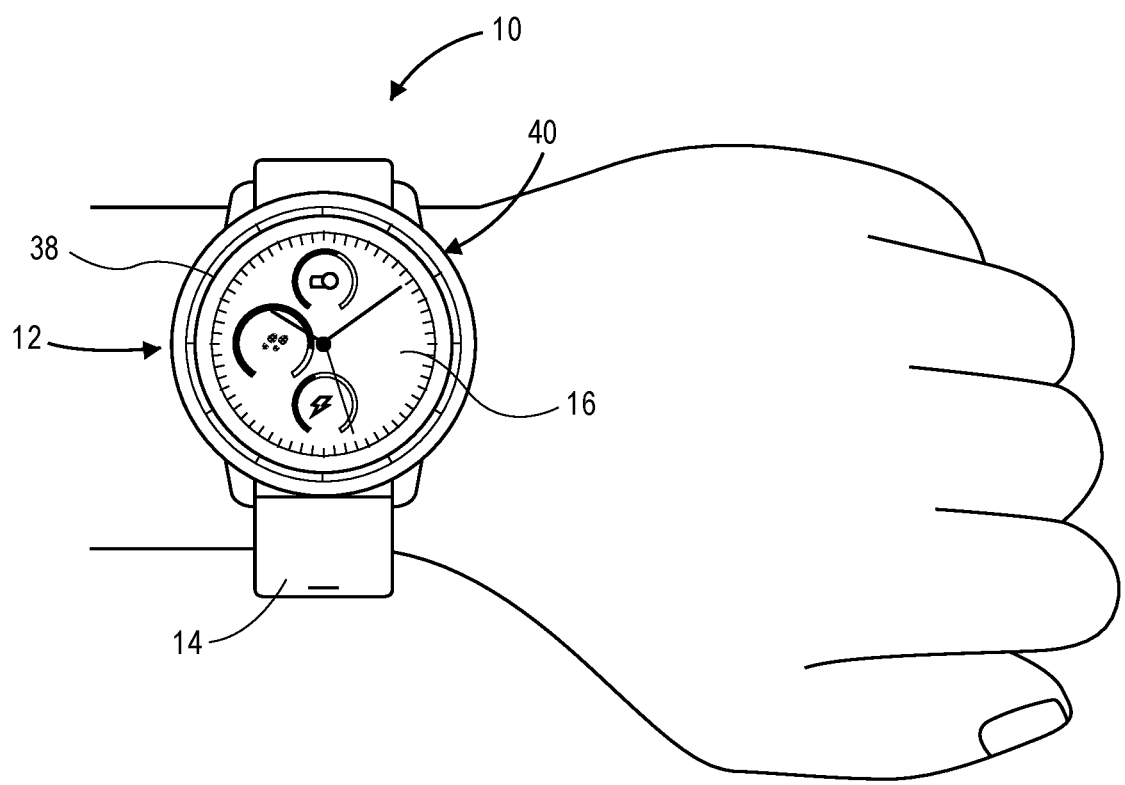
FIG. 1 is a top view of an electronic fitness device, constructed in accordance with various embodiments of the present technology, worn on a user's wrist.
Figure 2:
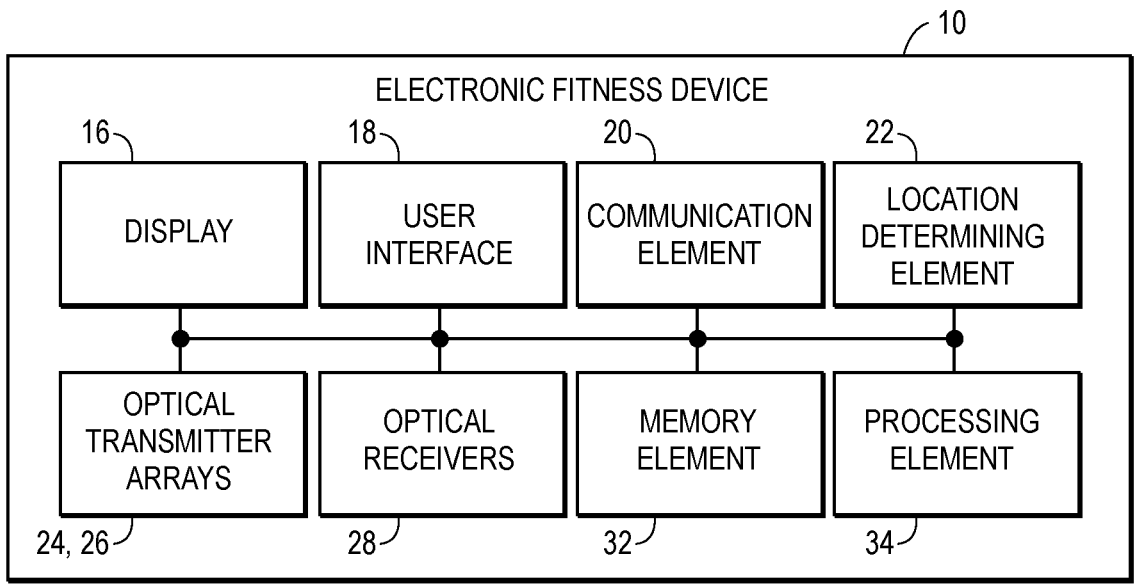
FIG. 2 is a schematic block diagram of various electronic components of the electronic fitness device.

The drawing figures do not limit the present technology to the specific embodiments disclosed and described herein. While the drawings do not necessarily provide exact dimensions or tolerances for the illustrated components or structures, the drawings are to scale as examples of certain embodiments with respect to the relationships between the components with the structures illustrated in the drawings.

DETAILED DESCRIPTION

The following detailed description of the technology references the accompanying drawings that illustrate specific embodiments in which the technology can be practiced. The embodiments are intended to describe aspects of the technology in sufficient detail to enable those skilled in the art to practice the technology. Other embodiments can be utilized and changes can be made without departing from the scope of the present technology. The following detailed description is, therefore, not to be taken in a limiting sense. The scope of the present technology is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

Embodiments of the present technology provide an electronic fitness device that may be worn on a user's wrist, such as the electronic fitness device shown in FIG. 1, and provides optical cardiac monitoring by generating and utilizing photoplethysmogram (PPG) signals. The use of PPG signals for optical cardiac monitoring, such as measuring a user's pulse or heart rate, a pulse oximetry ("Pulse Ox") level (also known as a level of blood oxygen saturation, or SpO2), an estimated stress level, a maximum rate of oxygen consumption (VO2 max), or the like. The electronic fitness device includes a first optical transmitter array and a second optical transmitter array, each of which is configured to output optical signals having a plurality of wavelengths. The optical signals pass through the user's skin and are received once they exit the user's skin by a plurality of optical receivers. Each optical receiver generates an electronic PPG signal for each optical signal received. The PPG signals are communicated to a processing element which processes the PPG signals to determine the user's heart rate or pulse oximetry.

In exemplary embodiments, the electronic fitness device includes four optical receivers positioned on a bottom wall of the electronic fitness device and oriented to form a quadrilateral shape with a space in the center of the quadrilateral. The first optical transmitter array is positioned in the space adjacent, or proximate, to two of the optical receivers. The second optical transmitter array is positioned in the space adjacent, or proximate, to the other two optical receivers. Hence, the first optical transmitter array is spaced apart from the second optical transmitter array along first and second orthogonal axes. This configuration of the optical transmitter arrays and the optical receivers provides signal diversity for the optical signals passing through the user's skin from the optical transmitter arrays to the optical receivers. Signal diversity includes having the optical signals travel different distances, through different angles, in different directions, and along different paths when passing through the user's skin. Signal diversity is beneficial because it allows for more accurate determination of the user's heart rate and pulse oximetry.

The configuration of the optical transmitter arrays and the optical receivers also provides improved performance when the electronic fitness device becomes tilted on the user's wrist, as may be likely when the user is exercising or working out. Prior art electronic fitness devices may have just one optical transmitter. When the electronic fitness device becomes tilted on the user's wrist, the optical transmitter becomes separated from the user's skin. Separation of the optical transmitter from the user's skin results in the optical signal level being greatly reduced when it is received by an optical receiver, which in turn generates a PPG signal with a relatively low signal to noise ratio (SNR). Consequently, the processing element may not be able to determine cardiac information from a PPG signal with a low SNR. Having the configuration of the present technology, with the first and second optical transmitter arrays spaced apart from one another along first and second orthogonal axes, results in one of the optical transmitter arrays making good contact with the user's skin if the other optical transmitter array gets separated from the user's skin when the electronic fitness device is tilted. And with good skin contact, the optical signal level will be relatively high, which results in the optical receivers generating PPG signals with a relatively high SNR. Given PPG signals with a high SNR, the processing element is able to determine the user's cardiac information.

Embodiments of the technology will now be described in more detail with reference to the drawing figures. Referring initially to FIGS. 1-8, an electronic fitness device 10 is illustrated. An exemplary electronic fitness device 10 may be embodied by a smart watch or a fitness band that is typically worn on a user's wrist, but may also be embodied by bands or belts worn on the user's arm, leg, head or torso. Other examples of the electronic fitness device 10 may include smartphones, personal data assistants, or the like which include a surface, operable to retain optical devices, that can be pressed against the user's skin. The electronic fitness device 10 may broadly comprise a housing 12, a wrist band 14, a display 16, a user interface 18, a communication element 20, a location determining element 22, a first optical transmitter array 24, a second optical transmitter array 26, a third optical transmitter array 27, a first optical receiver 28A, a second optical receiver 28B, a third optical receiver 28C, a fourth optical receiver 28D, a fifth optical receiver 28E, a sixth optical receiver 28F, a seventh optical receiver 28G, an eighth optical receiver 28H, a plurality of lenses 30, a memory element 32, and a processing element 34.

Figure 3:
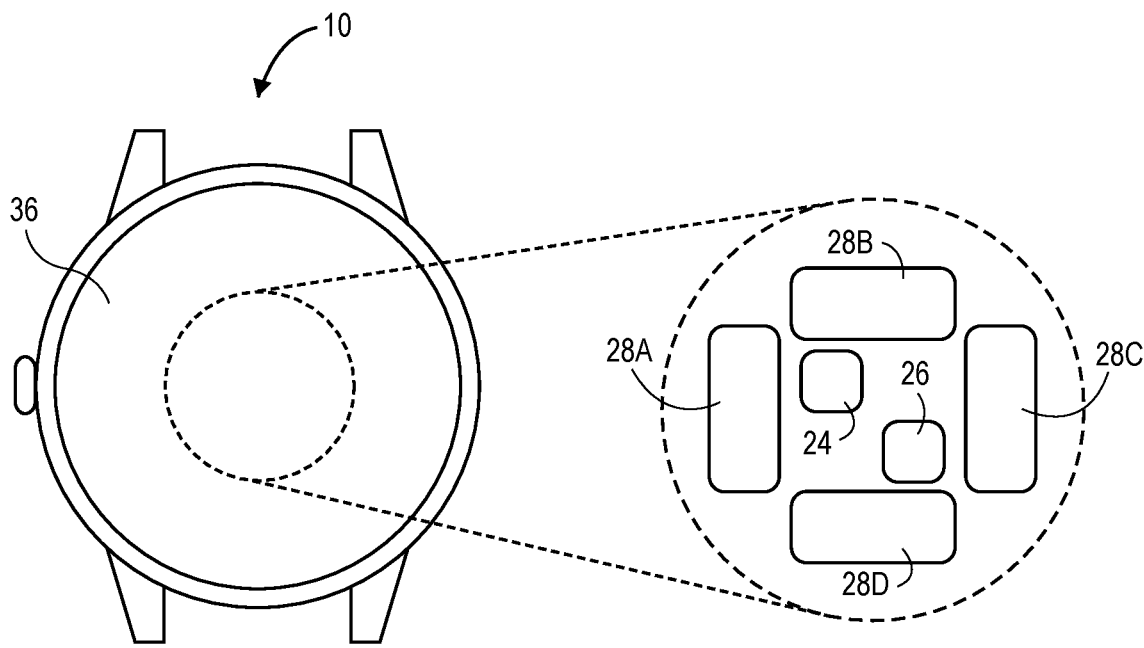
FIG. 3 is a bottom view of the electronic fitness device, illustrating a plurality of optical transmitter arrays and a plurality of optical receivers.

The housing 12 generally houses or retains other components of the electronic fitness device 10 and may include or be coupled to the wrist band 14. As seen in FIG. 3, the housing 12 may include a bottom wall 36, an upper surface 38, and at least one side wall 40 that bound an internal cavity (not shown in the figures). The bottom wall 36 includes a lower, outer surface that contacts the user's wrist while the user is wearing the electronic fitness device 10. The bottom wall 36 may be substantially flat with a slight curvature that enables the bottom wall 36 to contact a substantial portion of the user's wrist. The upper surface 38 opposes the bottom wall 36. In various embodiments, the upper surface 38 may further include an opening that extends from the upper surface to the internal cavity. In some embodiments, such as the exemplary embodiments shown in the figures, the bottom wall 36 of the housing 12 may have a round, circular, or oval shape, with a single circumferential side wall 40. In other embodiments, the bottom wall 36 may have a four-sided shape, such as a square or rectangle, or other polygonal shape, with the housing 12 including four or more sidewalls. The bottom wall 36 may include one or more openings in which the optical transmitter arrays 24, 26 and the optical receivers 28 are placed, positioned, or located. The one or more openings within the bottom wall 36 may be covered by one or more lenses 30 through which the optical signal may be transmitted and received.

The display 16 generally presents the information mentioned above, such as time of day, current location, and the like. The display 16 may be implemented in one of the following technologies: light-emitting diode (LED), organic LED (OLED), Light Emitting Polymer (LEP) or Polymer LED (PLED), liquid crystal display (LCD), thin film transistor (TFT) LCD, LED side-lit or back-lit LCD, or the like, or combinations thereof. In some embodiments, the display 16 may have a round, circular, or oval shape. In other embodiments, the display 16 may possess a square or a rectangular aspect ratio which may be viewed in either a landscape or a portrait orientation.

The user interface 18 generally allows the user to directly interact with the electronic fitness device 10 and may include pushbuttons, rotating knobs, or the like. In various embodiments, the display 16 may also include a touch screen occupying the entire display 16 or a portion thereof so that the display 16 functions as at least a portion of the user interface 18. The touch screen may allow the user to interact with the electronic fitness device 10 by physically touching, swiping, or gesturing on areas of the display 16.

The communication element 20 generally allows communication with external systems or devices. The communication element 20 may include signal and/or data transmitting and receiving circuits, such as antennas, amplifiers, filters, mixers, oscillators, digital signal processors (DSPs), and the like. The communication element 20 may establish communication wirelessly by utilizing radio frequency (RF) signals and/or data that comply with communication standards such as cellular 2G, 3G, 4G, LTE, or 5G, Institute of Electrical and Electronics Engineers (IEEE) 802.11 standard such as Wi-Fi, IEEE 802.16 standard such as WiMAX, Bluetooth™, or combinations thereof. In addition, the communication element 20 may utilize communication standards such as ANT, ANT+, Bluetooth™ low energy (BLE), the industrial, scientific, and medical (ISM) band at 2.4 gigahertz (GHz), or the like. Alternatively, or in addition, the communication element 20 may establish communication through connectors or couplers that receive metal conductor wires or cables which are compatible with networking technologies such as Ethernet. In certain embodiments, the communication element 20 may also couple with optical fiber cables. The communication element 20 may be in electronic communication with the memory element 32 and the processing element 34.

The location determining element 22 generally determines a current geolocation of the electronic fitness device 10 and may receive and process radio frequency (RF) signals from a multi-constellation global navigation satellite system (GNSS) such as the global positioning system (GPS) utilized in the United States, the Galileo system utilized in Europe, the GLONASS system utilized in Russia, or the like. The location determining element 22 may accompany or include an antenna to assist in receiving the satellite signals. The antenna may be a patch antenna, a linear antenna, or any other type of antenna that can be used with location or navigation devices. The location determining element 22 may include satellite navigation receivers, processors, controllers, other computing devices, or combinations thereof, and memory. The location determining element 22 may process a signal, referred to herein as a "location signal", from one or more satellites that includes data from which geographic information such as the current geolocation is derived. The current geolocation may include coordinates, such as the latitude and longitude, of the current location of the electronic fitness device 10. The location determining element 22 may communicate the current geolocation to the processing element 34, the memory element 32, or both.

Although embodiments of the location determining element 22 may include a satellite navigation receiver, it will be appreciated that other location-determining technology may be used. For example, cellular towers or any customized transmitting radio frequency towers can be used instead of satellites may be used to determine the location of the electronic fitness device 10 by receiving data from at least three transmitting locations and then performing basic tri-angulation calculations to determine the relative position of the device with respect to the transmitting locations. With such a configuration, any standard geometric triangulation algorithm can be used to determine the location of the electronic fitness device 10. The location determining element 22 may also include or be coupled with a pedometer, accelerometer, compass, or other dead-reckoning components which allow it to determine the location of the device 10. The location determining element 22 may determine the current geographic location through a communications network, such as by using Assisted GPS (A-GPS), or from another electronic device, such as a fitness device or a mobile device (e.g., smartphone). The location determining element 22 may even receive location data directly from a user.

The first optical transmitter array 24 outputs, transmits, or emits a plurality of optical signals that are to pass, or travel, through the user's skin and exit before being received by the optical receivers 28. The first optical transmitter array 24 includes a plurality of optical transmitters 42 (each optical transmitter 42 indicated in FIGS. 4A, 4B, 5A, and 6 with a "TX A" prefix). In some embodiments, each optical transmitter 42 may include a photonic generator, such as a light-emitting diode (LED), a modulator, a top emitter, an edge emitter, or the like. The photonic generator receives an electrical input signal from the processing element 34 that may be a control signal, such as an electric voltage or electric current that is analog or digital, or data, either of which is indicative of activating or energizing the optical transmitter 42 to output an optical signal having a desired amplitude, frequency, and duration. The photonic generator of each optical transmitter 42 transmits or outputs electromagnetic radiation having a particular wavelength (the optical signal) in the visible light spectrum, which is typically between approximately 400 nanometers (nm) to 700 nm, or in the infrared spectrum, which is typically between approximately 700 nm to 1 millimeter (mm). However, in some embodiments, the photonic generator transmits electromagnetic radiation in wavelength range of 1000 nm to 1500 nm. The wavelength of the optical signal is generally determined by, or varies according to, the material from which the photonic generator of each optical transmitter 42 is formed. The optical signal may comprise a sequence of pulses, a periodic or non-periodic waveform, a constant level for a given period of time, or the like, or combinations thereof. In other embodiments, each optical transmitter 42 may include a driver circuit, with electronic circuitry such as amplifier and an optional filter, electrically coupled to the photonic generator. The driver circuit may receive the electrical input signal (control signal) from the processing element 34 and the driver circuit may generate an electric voltage or electric current to the photonic generator, which in turn, outputs the optical signal.

An exemplary first optical transmitter array 24 includes a first optical transmitter 42A1 configured or operable to output an optical signal having a first wavelength ($\lambda 1$), a second optical transmitter 42A2 configured or operable to output an optical signal having a second wavelength ($\lambda 2$), and a third optical transmitter 42A3 configured or operable to output an optical signal having a third wavelength ($\lambda 3$). In other embodiments, the first optical transmitter array 24 may include a larger number of optical transmitters 42 or a smaller number of optical transmitters 42. The first wavelength $\lambda 1$ may range from approximately 540 nm to approximately 580 nm. The second wavelength $\lambda 2$ may range from approximately 620 nm to approximately 700 nm. The third wavelength $\lambda 3$ may range from approximately 850 nm to approximately 950 nm. The first wavelength $\lambda 1$ may be utilized to determine the user's heartrate. The second wavelength $\lambda 2$ and the third wavelength $\lambda 3$ may be utilized in combination to determine the user's pulse oximetry.

The optical transmitters 42 of first optical transmitter array 24 may be positioned relative to one another in any arrangement. For instance, in some embodiments (as shown in the figures), the optical transmitters 42 are positioned within the first optical transmitter array 24 with their centers equally spaced from one another in an equilateral triangle formation. In other embodiments, the optical transmitters 42 may be positioned with their centers aligned along a linear axis, such as along a horizontal axis or along a vertical axis, or in any arrangement in which the optical transmitters 42 are sufficiently spaced apart.

The second optical transmitter array 26 includes one or more optical transmitters 44 (each optical transmitter 44 indicated in FIGS. 4A, 4B, 5B and 6 with a "TX B" prefix) and is similar in structure, function, and operation to the first optical transmitter array 24 and transmits or emits a plurality of optical signals that are to pass, or travel, through the user's skin and exit before being received by the optical receivers 28. An exemplary second optical transmitter array 26 includes a first optical transmitter 44B1 configured or operable to output an optical signal having the first wavelength $\lambda 1$, a second optical transmitter 44B2 configured or operable to output an optical signal having the second wavelength $\lambda 2$, and a third optical transmitter 44B3 configured or operable to output an optical signal having the third wavelength $\lambda 3$. As with the first optical transmitter array 24, the wavelengths output by the second optical transmitter array 26 may be utilized to perform particular functions. That is, the first wavelength $\lambda 1$ may be utilized to determine the user's heartrate, while the second wavelength $\lambda 2$ and the third wavelength $\lambda 3$ may be utilized in combination to determine the user's pulse oximetry.

Figure 4A:
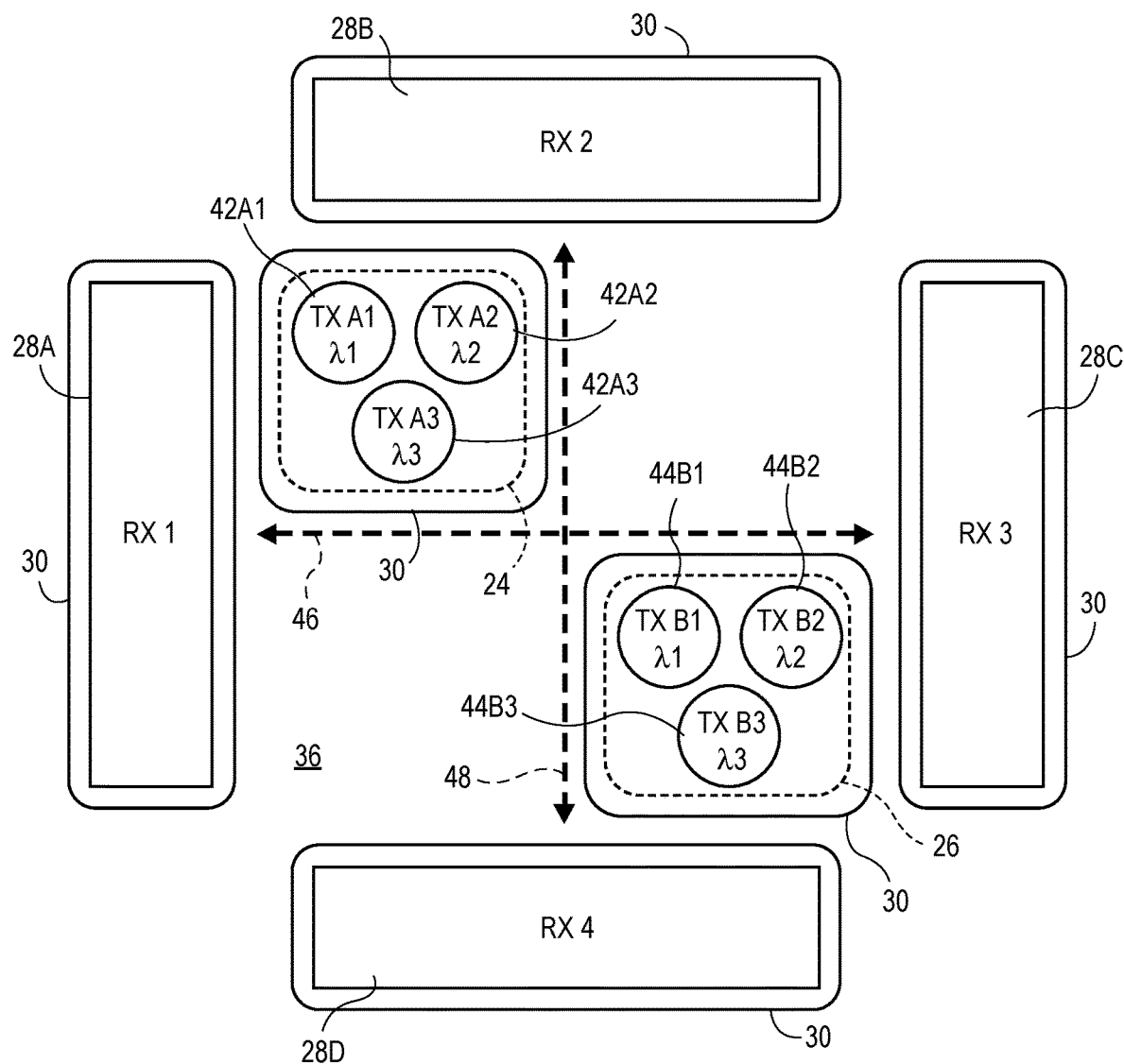
FIG. 4A is a schematic block diagram of a first embodiment of the optical transmitter arrays and the optical receivers.

The first optical transmitter array 24 is positioned at a first location, or in a first opening, on the bottom wall 36 of the housing 12, and the second optical transmitter array 26 is positioned at a second location, or in a second opening, on the bottom wall 36, as shown in FIGS. 3 and 4A. The first optical transmitter array 24 and the second optical transmitter array 26 are spaced apart from one another along a first axis 46 and along a second axis 48, orthogonal to the first axis 46, on the bottom wall 36. As shown in FIG. 4A, the first optical transmitter array 24 and the second optical transmitter array 26 are spaced apart from one another along the first axis 46, e.g., an X axis, and along the second axis 48, e.g., a Y axis, when viewing the bottom wall 36 as an XY plane. Accordingly, the first optical transmitter array 24 and the second optical transmitter array 26 may be considered to be positioned diagonal from one another. In some embodiments, additional transmitter arrays may be included (resulting in a total of four or more transmitter arrays) in a bottom wall 36 of housing 12. For example, the additional transmitter arrays may be positioned proximate to transmitter arrays 24 and 26.

Figure 4B:
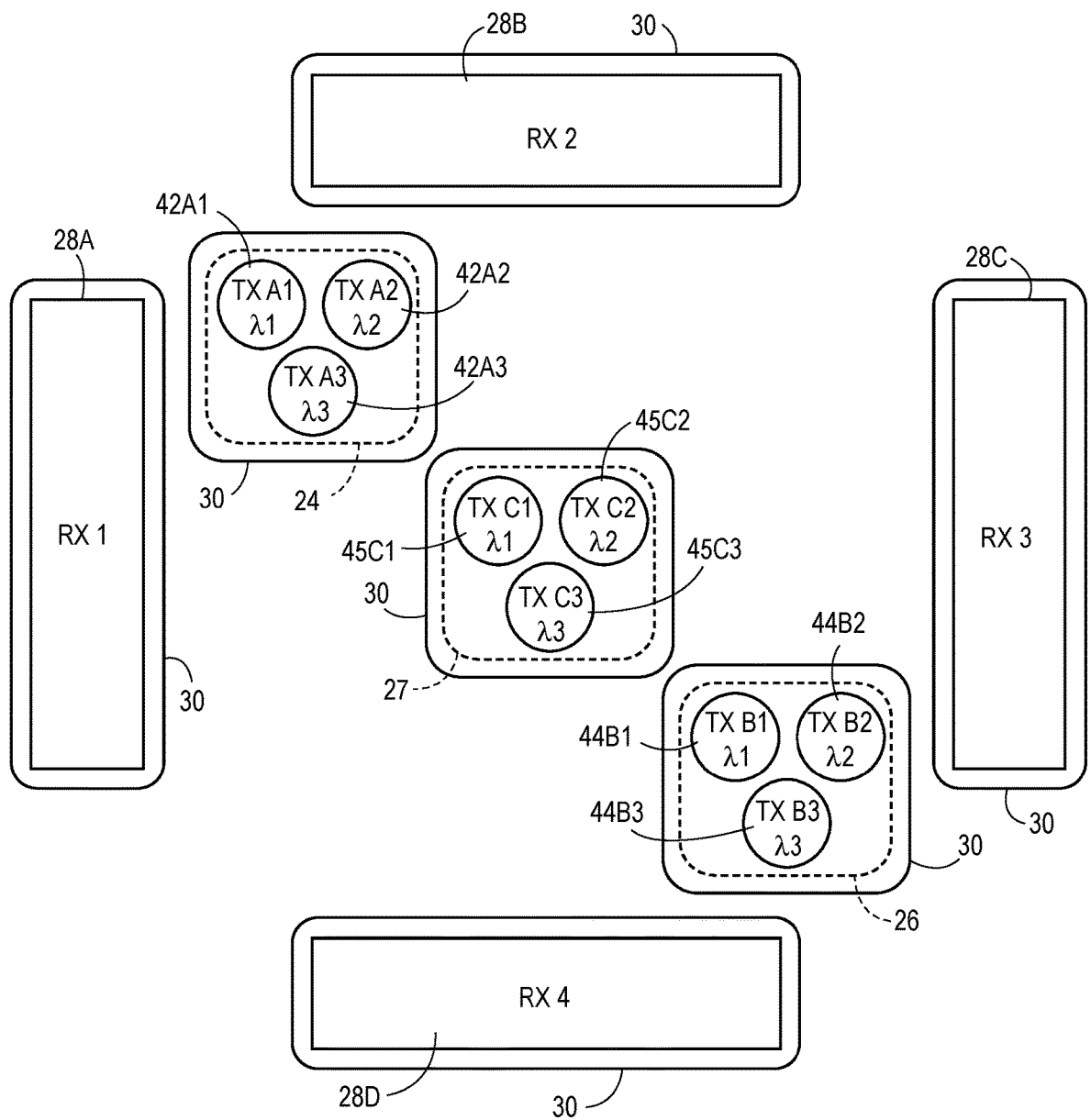
FIG. 4B is a schematic block diagram of a second embodiment of the optical transmitter arrays and the optical receivers.
Figure 5A:
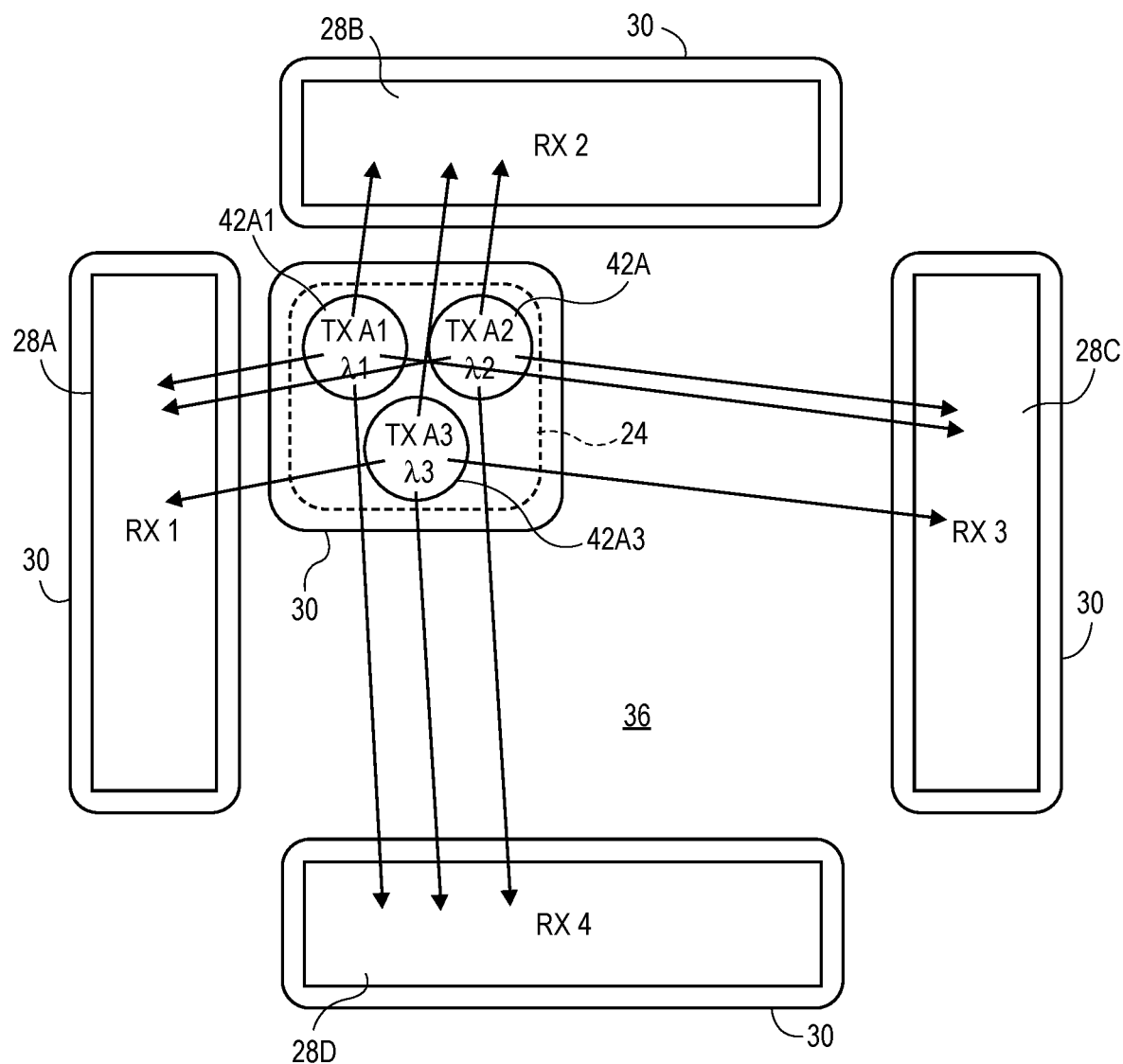
FIG. 5A is a schematic block diagram of a first optical transmitter array and the optical receivers illustrating signal paths for a plurality of optical signals.
Figure 5B:
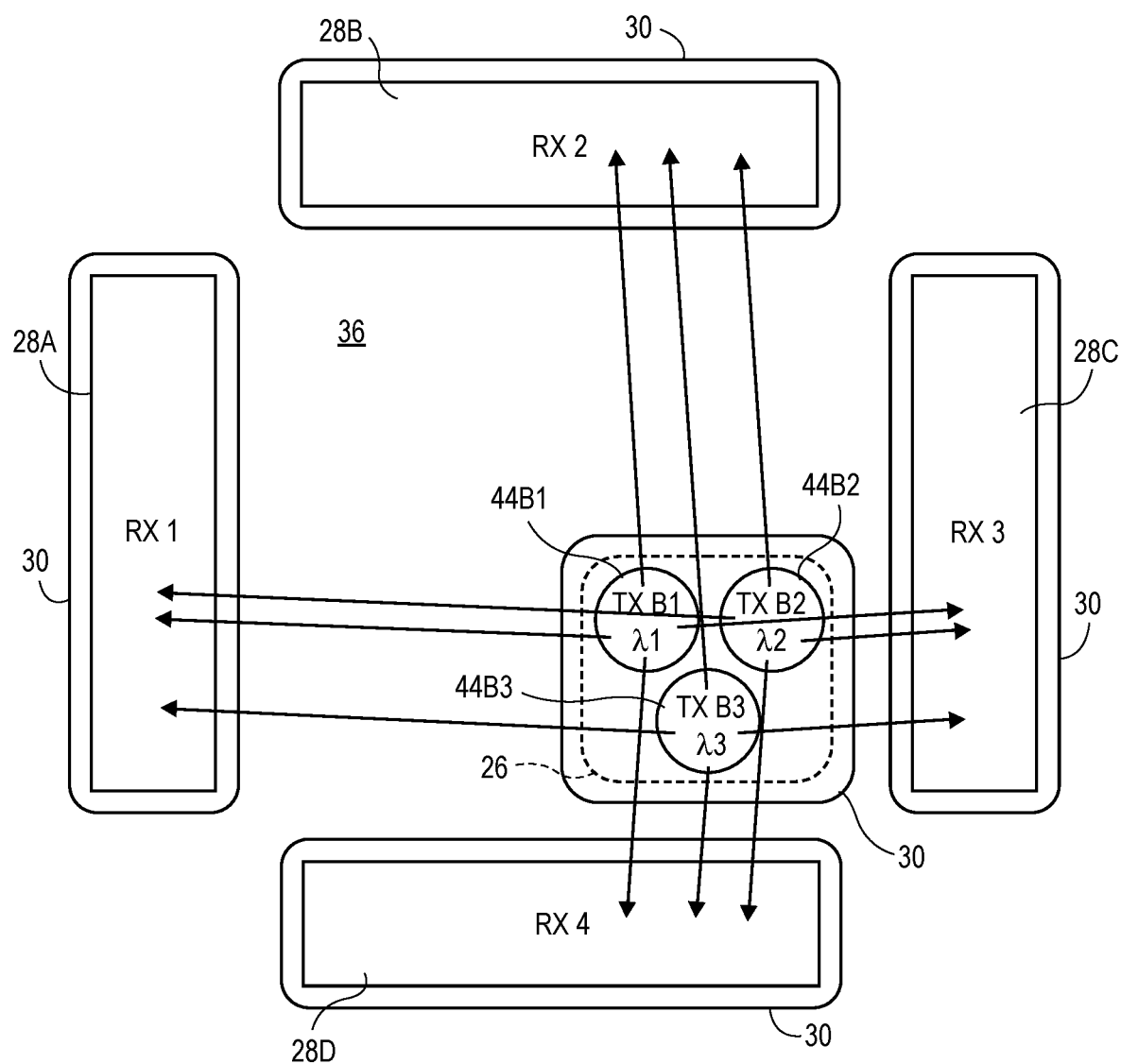
FIG. 5B is a schematic block diagram of a second optical transmitter array and the optical receivers illustrating signal paths for a plurality of optical signals.
Figure 5C:
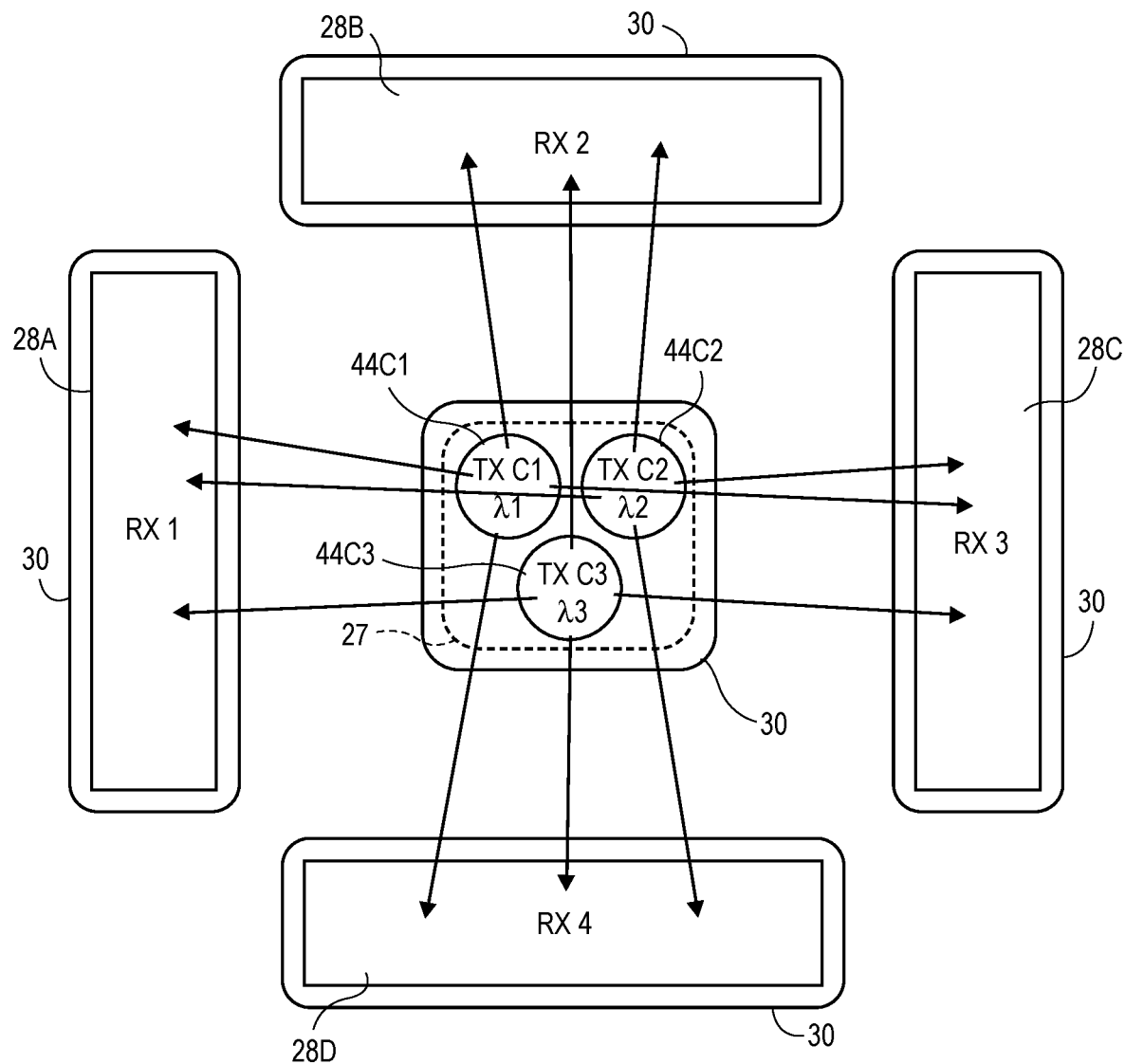
FIG. 5C is a schematic block diagram of a third optical transmitter array and the optical receivers illustrating signal paths for a plurality of optical signals.
Figure 6:
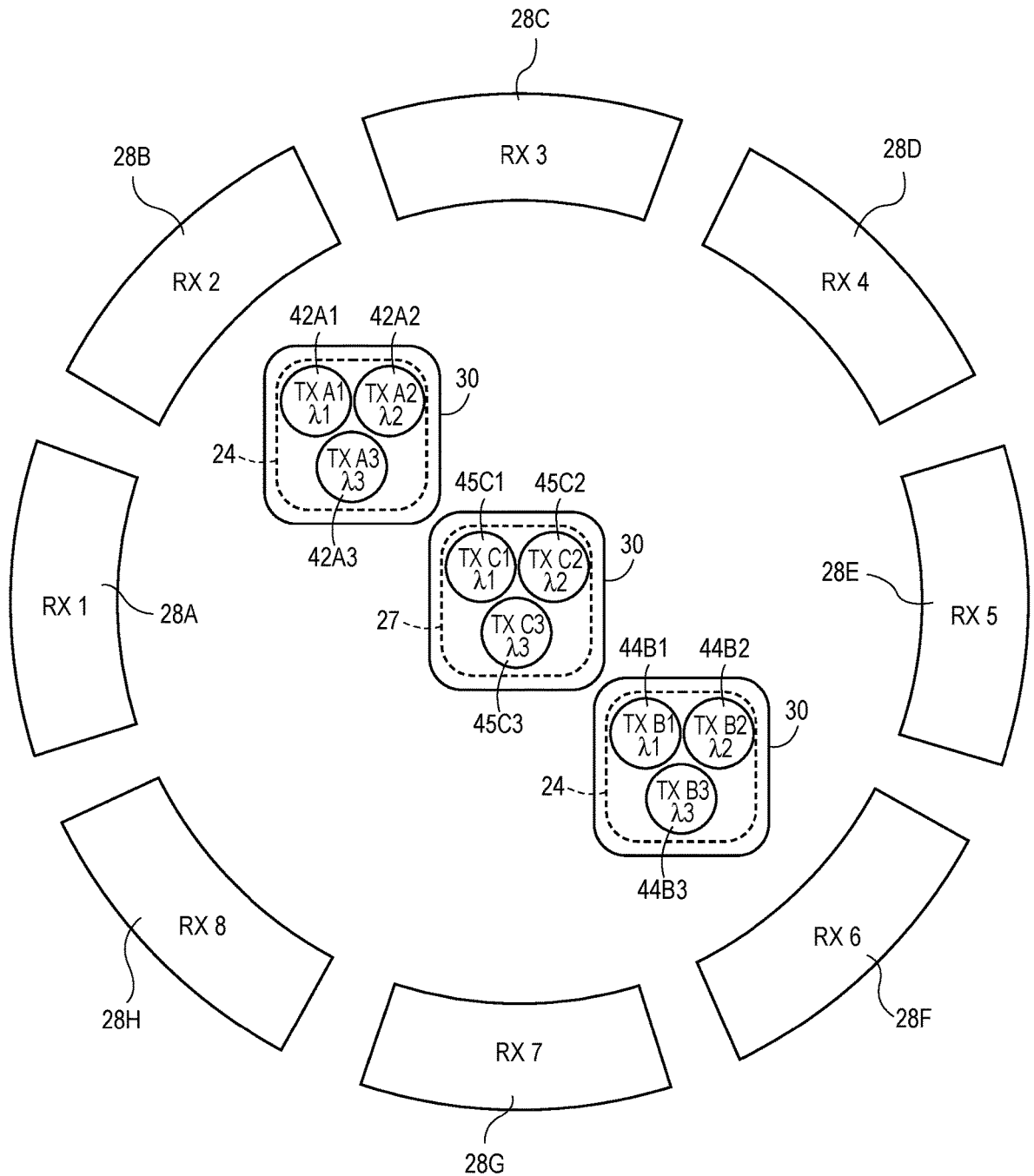
FIG. 6 is a schematic block diagram of a third embodiment of the optical transmitter arrays and the optical receivers.

In various embodiments, the electronic fitness device 10 comprises a third optical transmitter array 27 including a plurality of optical transmitters 45 (each optical transmitter 45 indicated in FIGS. 4B, 5C, and 6 with a "TX C" prefix). The third optical transmitter array 27 is similar in structure, function, and operation to the first optical transmitter array 24 and transmits or emits a plurality of optical signals that are to pass, or travel, through the user's skin and exit before being received by the optical receivers 28. An exemplary third optical transmitter array 27 includes a first optical transmitter 45C1 configured or operable to output an optical signal having the first wavelength $\lambda 1$, a second optical transmitter 45C2 configured or operable to output an optical signal having the second wavelength λ2, and a third optical transmitter 45C3 configured or operable to output an optical signal having the third wavelength λ3.

Referring to FIG. 4B, the third optical transmitter array 27 is positioned at a third location, or in a third opening, on the bottom wall 36 of the housing 12 between the first optical transmitter array 24 and the second optical transmitter array 26 so that the center of each array 24, 26, 27 lies along a diagonal line. Thus, the third optical transmitter array 27 is spaced apart from the first optical transmitter array 24 and the second optical transmitter array 26 along the first axis 46 and along the second axis 48. The third optical transmitter array 27 may be positioned approximately midway between the first optical transmitter array 24 and the second optical transmitter array 26 along the first axis 46 and along the second axis 48. In some embodiments, the third optical transmitter array 27 may be positioned roughly in the center of the bottom wall 36.

The first optical receiver 28A, the second optical receiver 28B, the third optical receiver 28C, and the fourth optical receiver 28D (indicated in FIGS. 4A, 4B, 5A, 5B, and 5C with an "RX" prefix) each receive optical signals that have passed, or traveled, through the user's skin. In some embodiments, each optical receiver 28 may include a photodetector, such as a photodiode, a phototransistor, a photoresistor, a phototube, or the like. The photodetector receives electromagnetic radiation having multiple wavelengths (typically any of the wavelengths generated by the photonic generators) and in response, generates an electronic PPG signal, comprising an electric current, an electric voltage, or other electrical parameter, that corresponds to the intensity of the modulated optical signal in amplitude and frequency that is transmitted by one of the optical transmitters 42 and reflected from (after passing or traveling through) the user's skin. Given that the optical receivers 28 may receive multiple optical signals, each having a particular wavelength, each PPG signal generated by any optical receiver 28 may be a particular wavelength-related PPG signal because it includes characteristics or components resulting from, or related to, the particular wavelength of the optical signal output by an optical transmitter 42 of the first or second optical transmitter arrays 24, 26. In other embodiments, each optical receiver 28 may include the photodetector electrically coupled to an amplifier circuit followed by an analog-to-digital converter (ADC). The photodetector may receive electromagnetic radiation having multiple wavelengths and in response, may generate an output signal, comprising an electric current, an electric voltage, or other electrical parameter that corresponds to the intensity of the modulated optical signal in amplitude and frequency that is transmitted by an optical transmitter 42 and reflected from the user's skin. The amplifier circuit may receive the output signal from the photodetector and amplify it to produce an amplified output signal that is analog and communicated to the ADC. The ADC may sample the amplified output signal and output a PPG signal, which is converted into a corresponding stream of digital data.

Each optical receiver 28 may have a rectangular shape with an elongated aspect ratio wherein a length of each optical receiver 28 is much greater than a width of each optical receiver 28. Alternatively, each optical receiver 28 may have a square shape, a circular shape, and oval shape, or any one of a plurality of other geometric shapes. In embodiments, receivers 28 form a circle, ring or polygon around transmitter arrays 24 and 26, with the ring being partitioned into 4 or more separate receivers 28.

Referring to FIGS. 3, 5A, 5B, and 5C, the first optical receiver 28A is positioned at a third location, or in a third opening, on the bottom wall 36 of the housing 12. The second optical receiver 28B is positioned at a fourth location, or in a fourth opening, on the bottom wall 36. The third optical receiver 28C is positioned at a fifth location, or in a fifth opening, on the bottom wall 36. The fourth optical receiver 28D is positioned at a sixth location, or in a sixth opening, on the bottom wall 36. If the third optical transmitter array 27 is included with the electronic fitness device 10, then the first optical receiver 28A is positioned at a fourth location, or in a fourth opening, the second optical receiver 28B is positioned at a fifth location, or in a fifth opening, the third optical receiver 28C is positioned at a sixth location, or in a sixth opening, and the fourth optical receiver 28D is positioned at a seventh location, or in a seventh opening. The first optical receiver 28A is aligned with, and spaced apart from, the third optical receiver 28C along the first axis 46 of the bottom wall 36. The second optical receiver 28B is aligned with, and spaced apart from, the fourth optical receiver 28D along the second axis 48. The optical receivers 28 may be positioned and oriented such that they form a quadrilateral (roughly square) area between them centered roughly in a center of the bottom wall 36, wherein the first optical receiver 28A may be oriented at a 180-degree angle relative to the center of the bottom wall 36, the second optical receiver 28B may be oriented at a 90-degree angle, the third optical receiver 28C may be oriented at a 0-degree angle, and the fourth optical receiver 28D may be oriented at a 270-degree angle. However, it is to be understanding the arrangement depicted in at least FIG. 3 may be rotated 90-degrees to form a diamond pattern, where the first optical transmitter array 24 is positioned above the second optical transmitter array 26 and the first optical receiver 28A is positioned approximately 45 degrees of rotation from a center point from an axis extending to the top of the bottom wall 36, the second optical receiver 28B is positioned approximately 135 degrees of rotation from said point, the third optical receiver 28C is positioned approximately 225 degrees of rotation from said point, and the fourth optical receiver 28D is positioned approximately 315 degrees of rotation from said point. Furthermore, the optical receivers 28 are positioned such that they surround the first optical transmitter array 24 and the second optical transmitter array 26. That is, the first optical receiver 28A faces a first side of the first optical transmitter array 24 and the second optical transmitter array 26. The second optical receiver 28B faces a second side of the first optical transmitter array 24 and the second optical transmitter array 26. The third optical receiver 28C faces a third side of the first optical transmitter array 24 and the second optical transmitter array 26. The fourth optical receiver 28D faces a fourth side of the first optical transmitter array 24 and the second optical transmitter array 26.

Referring to FIG. 6, in various embodiments, the electronic fitness device 10 comprises a fifth optical receiver 28E, a sixth optical receiver 28F, a seventh optical receiver 28G, and an eighth optical receiver 28H (indicated as "RX5", "RX6", RX7", and "RX8") similar in function and operation to the optical receivers 28A-28D described above. In such embodiments, the optical receivers 28A-28D are repositioned from the locations described above and shown in FIGS. 4A, 4B, 5A, 5B, and 5C. The optical receivers 28A-28H are positioned in openings, or at locations, on the bottom wall 36 along a circumference of a circular formation at angular intervals of approximately 45 degrees. The optical transmitter arrays 24, 26, 27 are positioned in the area on the bottom wall 36 bounded by the optical receivers 28. Each optical receiver 28 has a roughly annular sector shape, with side walls that are arcuate in shape or shaped like a portion of a circumference of one of two circles, and end walls shaped roughly like a portion of a radius of the circular formation of the optical receivers 28. Each receiver 28 is also configured to receive optical signals from each of the optical transmitter arrays 24, 26, 27 and generate a corresponding PPG signal.

The lenses 30, as shown in FIGS. 4A, 4B, 5A, 5B, and 5C, generally provide cover for the optical transmitter arrays 24, 26 and the optical receivers 28. In addition, the lenses 30 may be configured, operable, shaped, or formed to provide focusing, collimation, refraction, diffraction, and so forth. Furthermore, some lenses 30, such as the lenses 30 that cover the optical transmitter arrays 24, 26, may provide some functions, while other lenses 30, such as the lenses 30 that cover the optical receivers 28, may provide other functions. The lenses 30 that cover the optical transmitter arrays 24, 26 may direct optical signals transmitted by the optical transmitters 42, 44 to the skin of the user. The lenses 30 that cover the optical receivers 28 may direct the optical signals exiting from the skin to the optical receivers 28.

The memory element 32 may be embodied by devices or components that store data in general, and digital or binary data in particular, and may include exemplary electronic hardware data storage devices or components such as read-only memory (ROM), programmable ROM, erasable programmable ROM, random-access memory (RAM) such as static RAM (SRAM) or dynamic RAM (DRAM), cache memory, hard disks, floppy disks, optical disks, flash memory, thumb drives, universal serial bus (USB) drives, or the like, or combinations thereof. In some embodiments, the memory element 32 may be embedded in, or packaged in the same package as, the processing element 34. The memory element 32 may include, or may constitute, a non-transitory "computer-readable medium". The memory element 32 may store the instructions, code, code statements, code segments, software, firmware, programs, applications, apps, services, daemons, or the like that are executed by the processing element 34. The memory element 32 may also store data that is received by the processing element 34 or the device in which the processing element 34 is implemented. The processing element 34 may further store data or intermediate results generated during processing, calculations, and/or computations as well as data or final results after processing, calculations, and/or computations. In addition, the memory element 32 may store settings, data, documents, sound files, photographs, movies, images, databases, and the like. In various embodiments, the memory element 32 may store parameters such as threshold values and the like, which are retrieved during the operation of the electronic fitness device 10.

The processing element 34 may comprise one or more processors. The processing element 34 may include electronic hardware components such as microprocessors (single-core or multi-core), microcontrollers, digital signal processors (DSPs), field-programmable gate arrays (FPGAs), analog and/or digital application-specific integrated circuits (ASICs), or the like, or combinations thereof. The processing element 34 may generally execute, process, or run instructions, code, code segments, code statements, software, firmware, programs, applications, apps, processes, services, daemons, or the like. The processing element 34 may also include hardware components such as registers, finite-state machines, sequential and combinational logic, and other electronic circuits that can perform the functions necessary for the operation of the current invention. In certain embodiments, the processing element 34 may include multiple computational components and functional blocks that are packaged separately but function as a single unit. The processing element 34 may be in electronic communication with the other electronic components through serial or parallel links that include universal busses, address busses, data busses, control lines, and the like.

The processing element 34 may be operable, configured, or programmed to perform the following functions by utilizing hardware, software, firmware, or combinations thereof. The processing element 34 generates the electrical input signal or control signal, which may include an electric voltage or electric current that is constant or variable, analog or digital, or data, as a single number or a stream of numbers, and communicates the signal to one of either the first optical transmitter array 24 or the second optical transmitter array 26, in a normal operating mode. However, in other modes of operation, such as a test mode, the processing element 34 is operable to communicate the electrical input signal or control signal to each optical transmitter 42, 44 individually at different times, to one or more groups of the optical transmitters 42, 44 simultaneously, or to all of the optical transmitters 42, 44 simultaneously. Thus, the processing element 34 may generate and transmit six electrical input signals or control signals, one for each optical transmitter 42, 44.

The processing element 34 generates and communicates the electrical input signal or control signal to the first optical transmitter array 24 or the second optical transmitter array 26 according to, or depending on, a signal to noise ratio (SNR) of the PPG signals generated by the optical receivers 28. Each optical receiver 28 generates the PPG signal resulting from the receipt of the optical signal from either the first optical transmitter array 24 or the second optical transmitter array 26. And, the PPG signal has an SNR which varies according to numerous factors, such as the distance between the bottom wall 36 and the user's skin. The SNR is generally inversely proportional to the distance between the bottom wall 36 and the user's skin. For example, a greater distance, or separation, between the bottom wall 36 and the user's skin results in a lower SNR. If the SNR of the PPG signals from both the first optical transmitter array 24 and the second optical transmitter array 26 are above an SNR threshold, then the processing element 34 may generate and communicate the electrical input signal or control signal to the first optical transmitter array 24 by default. If the SNR of the PPG signals of one of the first optical transmitter array 24 or the second optical transmitter array 26 is above the SNR threshold and the SNR of the PPG signals of the other one is not, then the processing element 34 may generate and communicate the electrical input signal or control signal to the optical transmitter array 42, 44 whose SNR of the PPG signals is above the SNR threshold. If the SNR of the PPG signals of neither the first optical transmitter array 24 nor the second optical transmitter array 26 is above the SNR threshold (perhaps as a result of the electronic fitness device 10 not being worn), then the processing element 34 may not generate and communicate the electrical input signal or control signal to either optical transmitter array 42, 44.

The processing element 34 generates and communicates the electrical input signal or control signal to a particular transmitter within either the first optical transmitter array 24 or the second optical transmitter array 26 according to, or based on, the function or operation that is requested to be performed. If a heart rate determination is requested, then the processing element 34 generates and communicates the electrical input signal or control signal for a first time period to the first optical transmitter 42A1 of the first optical transmitter array 24 or the first optical transmitter 44B1 of the second optical transmitter array 26, depending on conditions discussed above. The processing element 34 may pause for a second time period. The processing element 34 may then repeat the generation and communication of the electrical input signal or control signal followed by a pause.

If a pulse oximetry determination is requested, then the processing element 34 generates and communicates the electrical input signal or control signal for the first time period to the second optical transmitter 42A2 of the first optical transmitter array 24 or the second optical transmitter 44B2 of the second optical transmitter array 26. The processing element 34 may pause for a second time period. Then, the processing element 34 generates and communicates the electrical input signal or control signal for a third time period to the third optical transmitter 42A3 of the first optical transmitter array 24 or the third optical transmitter 44B3 of the second optical transmitter array 26. The processing element 34 may pause for a fourth time period. The processing element 34 may then repeat the sequence of generating and communicating of the electrical input signal or control signal to the second optical transmitter 42A2, 44B2, pausing, generating and communicating of the electrical input signal or control signal to the third optical transmitter 42A3, 44B3, and pausing in a time division multiplexing (TDM) fashion.

The processing element 34 receives the PPG signal from each of the optical receivers 28. As indicated in FIGS. 5A, 5B, 5C, and 7, each optical transmitter 42, 44 outputs, generates, transmits, or emits electromagnetic radiation, that is, the optical signal, omnidirectionally. Alternatively, a focused optical signal is scattered omnidirectionally by the user's skin. Thus, whenever any single optical transmitter 42, 44 outputs the optical signal, each of the optical receivers 28 receives the optical signal, assuming the bottom wall 36 is in good contact with the user's skin and the optical signal is passing through the user's skin. Accordingly, each optical receiver 28 generates and communicates the PPG signal whenever any optical transmitter 42, 44 outputs the optical signal. As a result, the processing element 34 receives a first PPG signal from the first optical receiver 28A, a second PPG signal from the second optical receiver 28B, a third PPG signal from the third optical receiver 28C, and a fourth PPG signal from the fourth optical receiver 28D. In embodiments that include the fifth through the eighth optical receivers 28E-28H, the processing element 34 receives a fifth PPG signal from the fifth optical receiver 28E, a sixth PPG signal from the sixth optical receiver 28F, a seventh PPG signal from the seventh optical receiver 28G, and an eighth PPG signal from the eighth optical receiver 28H.

The processing element 34 may condition the PPG signals by performing actions such as amplifying, filtering, averaging, or the like, or combinations thereof. Then, the processing element 34 may extract data from the PPG signals and determine or calculate the user's heart rate or pulse oximetry, depending on which cardiac monitoring value was requested. Furthermore, the processing element 34 may determine the SNR of each PPG signal individually or may determine the SNR of the average of two or more PPG signals. The processing element 34 may compare the SNR to the SNR threshold in order to determine to which optical transmitter array 24, 26 to communicate the electrical input signal or control signal.

In embodiments that include the third optical transmitter array 27, the processing element 34 may generate and communicate the electrical input signal or control signal to the third optical transmitter array 27 if the SNR of the PPG signals from the optical receivers 28 which resulted from the first optical transmitter array 24 or the second optical transmitter array 26 is below the SNR threshold. Additionally, or alternatively, the processing element 34 may generate and communicate the electrical input signal or control signal to the third optical transmitter array 27 as part of a sequence of generating and communicating the electrical input signal or control signal in a TDM fashion, or based on other criteria.

The electronic fitness device 10 may operate as follows. The user may desire to determine his cardiac information, such as heart rate or pulse oximetry. He may utilize the user interface 18 to direct the processing element 34 to begin the process of determining the heart rate and/or the pulse oximetry. Alternatively, or additionally, the processing element 34 may have an operating mode in which it automatically initiates the process of determining the heart rate or pulse oximetry when a predetermined event occurs (e.g., heart-rate variability exceeding a predetermined threshold, body temperature exceeding a predetermined threshold, etc.) or on a periodic basis (e.g., every second, every minute, hourly, daily, etc.).

Figure 7:
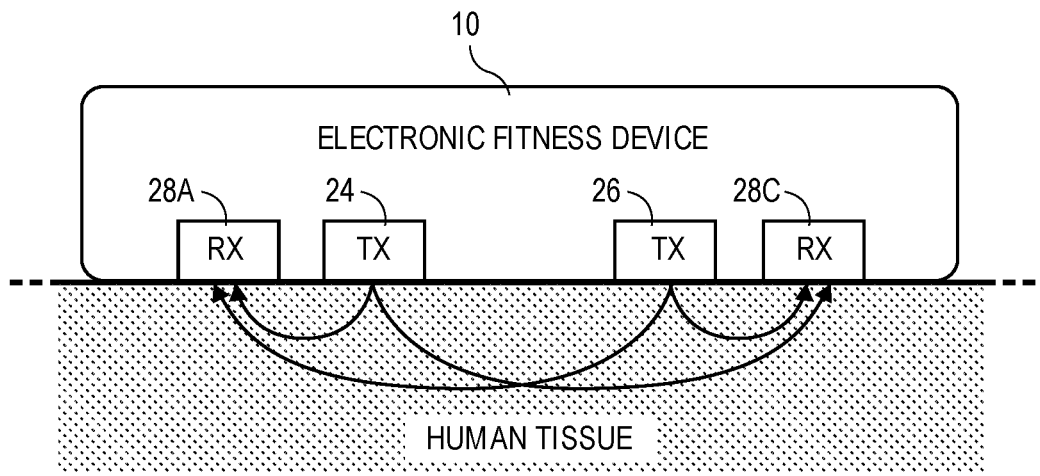
FIG. 7 is a schematic cross section of the electronic fitness device while being worn flush against the user's wrist.

The processing element 34 generates and communicates the electrical input signal or control signal to one of the optical transmitters 42, 44 in one of the optical transmitter arrays 24, 26. The particular optical transmitter 42, 44 and the particular optical transmitter array 24, 26 vary according to, or depend on, which cardiac parameter is requested and the value of the SNR of the PPG signals resulting from the optical signal from each of the optical transmitter arrays 24, 26. When the bottom wall 36 is uniformly flush against the user's skin as shown in FIG. 7, the processing element 34 may generate and communicate the electrical input signal or control signal to one of the optical transmitters 42, 44 in either of the optical transmitter arrays 24, 26, although the first optical transmitter array 24 may be chosen by default. The optical transmitter 42 outputs the optical signal which passes or travels through the user's skin and exits. Upon exit, the optical signal is received by each of the optical receivers 28, and each optical receiver 28 generates and communicates the PPG signal to the processing element 34. The processing element 34 receives the PPG signals and conditions them and processes them to determine the requested cardiac parameter.

Having the optical signal pass through the user's skin and travel in different directions, at different angles, along different paths, and over different distances before it is received by the optical receivers 28 helps to satisfy the goal of providing signal diversity of the optical signal—which in turn, leads to a more accurate determination of the user's heart rate and pulse oximetry. In exemplary embodiments, the optical signal output by each optical transmitter 42, 44 travels in four different directions, at four different angles, along four different paths, and over four different distances through the user's skin before it is received by the optical receivers 28.

Figure 8:
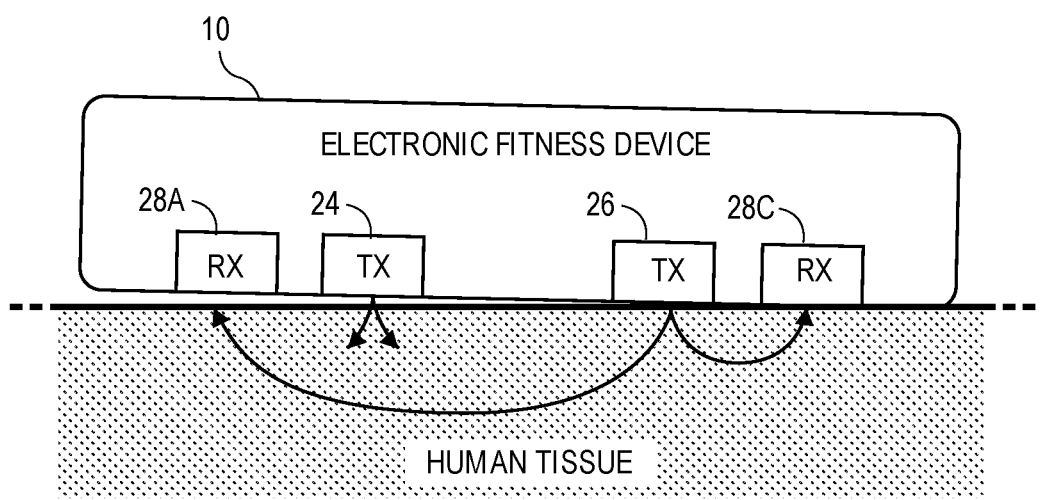
FIG. 8 is a schematic cross section of the electronic fitness device while being worn and tilted on the user's wrist.

During the course of exercising, or from normal activity and movement of the user's arm, the bottom wall 36 of the housing 12 may become tilted on the user's wrist so that it is no longer flush, as shown in FIG. 8. In this case, one of the optical transmitter arrays 24, 26 and/or one or more of the optical receivers 28 may become separated by a small distance, at least, from the user's skin. In such a case, the separated optical receivers 28 may receive the optical signal that has passed through the skin at a relatively much lower signal level or optical intensity. Perhaps more importantly, the optical signal output by the separated optical transmitter array 24, 26 does not launch into the skin properly, and some of the optical signal may be reflected by the surface of the user's skin—preventing proper penetration of the optical signal into the user's skin. Thus, the PPG signals generated by the optical receivers 28 which result from the optical signal from the separated optical transmitter array 24 likely have a very low SNR. The processing element 34 receives the PPG signals and determines whether the SNR is above the SNR threshold. If the SNR of the PPG signals is not above the SNR threshold, then the processing element 34 generates and communicates the electrical input signal or control signal to only the optical transmitter array 24, 26 which is not separated from the user's skin.

Having the first optical transmitter array 24 and the second optical transmitter array 26 separated from one another along first and second orthogonal axes along the bottom wall 36 of the housing 12 results in at least one of the optical transmitter arrays 24, 26 making good contact with the user's skin when the electronic fitness device 10 becomes tilted on the user's wrist. One of the optical transmitter arrays 24, 26 will make good contact with the user's skin no matter whether the electronic fitness device 10 becomes tilted along the first axis, such as sideways on the user's wrist, or along the second axis, such as lengthwise on the user's wrist. Furthermore, having the optical receivers 28 positioned such that each of the optical transmitter arrays 24, 26 is adjacent and/or proximate to two of the optical receivers 28 results in the optical transmitter array 24, 26 that makes good contact with the user's skin being able to communicate with at least two of the optical receivers 28. This configuration of the optical transmitter arrays 24, 26 and the optical receivers 28 ensures signal diversity even when the electronic fitness device 10 is tilted on the user's wrist and provides robust operation of the electronic fitness device 10 during intense physical activity.

In embodiments that include the third optical transmitter array 27, the electronic fitness device 10 may operate in a similar fashion as described above, except that the third optical transmitter 27 may be utilized if the other two optical transmitter arrays 24, 26 are not making good contact with the user's skin or if otherwise the SNR of the PPG signals originating from the other two optical transmitter arrays 24, 26 are below the SNR threshold. Additionally, or alternatively, the third optical transmitter array 27 may be utilized as part of a sequence of utilizing each of the optical transmitter arrays 24, 26, 27 in a TDM fashion, or as part of other schema.

In embodiments that include eight optical receivers 28, each optical receiver 28 is configured to receive optical signals from each of the optical transmitter arrays 24, 26, 27 and generate a corresponding PPG signal. Having eight optical receivers 28 positioned in a circular formation at 45-degree increments around the optical transmitter arrays 24, 26, 27 provides even greater diversity of the optical signal traveling through the user's skin from the source to the destination. Thus, there is the potential for the optical signal to travel in eight different directions, at eight different angles, along eight different paths, and over eight different distances through the user's skin.

Although the technology has been described with reference to the embodiments illustrated in the attached drawing figures, it is noted that equivalents may be employed and substitutions made herein without departing from the scope of the technology as recited in the claims.

Having thus described various embodiments of the technology, what is claimed as new and desired to be protected by Letters Patent includes the following:

What is claimed is:
1. An electronic fitness device comprising:
   a housing including a bottom wall configured to contact a user's wrist;
   a first optical transmitter array positioned at a first location on the bottom wall and operable to output a plurality of optical signals that pass through a user's skin, each optical signal having a unique wavelength;
   a first optical receiver positioned at a second location on the bottom wall and operable to receive the optical signals from the first optical transmitter array such that the optical signals travel along a first signal path and a first distance from the first optical transmitter array to the first optical receiver; and
   a second optical receiver positioned at a third location on the bottom wall and operable to receive the optical signals from the first optical transmitter array such that the optical signals travel along a second signal path and a second distance from the first optical transmitter array to the second optical receiver, wherein the second signal path is roughly orthogonal to the first signal path and the second distance is different from the first distance;
   wherein the first optical receiver is spaced apart from the first optical transmitter array along a first axis, and the second optical receiver is spaced apart from the first optical transmitter array along a second axis, the second axis orthogonal to the first axis, on the bottom wall.

2. The electronic fitness device of claim 1, wherein each optical receiver is operable to generate an electronic signal corresponding to the plurality of optical signals output by the first optical transmitter array.

3. The electronic fitness device of claim 2, wherein the electronic fitness device further comprises:
   a memory element configured to store a signal to noise ratio threshold; and
   a processing element coupled with the memory element and each of the optical receivers,
     the processing element configured to:
     receive the electronic signals from each of the optical receivers,
     determine a signal to noise ratio of each electronic signal,
     process the electronic signals having a determined signal to noise ratio is above the signal to noise threshold.

4. The electronic fitness device of claim 1, wherein the first optical receiver and the second optical receiver each have an elongated aspect ratio.

5. The electronic fitness device of claim 1, further comprising
   a second optical transmitter array positioned at a fourth location on the bottom wall and operable to output a plurality of optical signals that pass through the user's skin, each optical signal having a wavelength equal to a wavelength of a corresponding optical signal of the first optical transmitter array,
   wherein the first optical transmitter array and the second optical transmitter array are spaced apart from one another along the first axis and along the second axis on the bottom wall.

6. The electronic fitness device of claim 5, further comprising a third optical receiver positioned at a fifth location on the bottom wall and operable to receive the optical signals from the first optical transmitter array and the second optical transmitter array, the third optical receiver spaced apart from the first optical receiver with the first optical transmitter array and the second optical transmitter array positioned therebetween, and a fourth optical receiver positioned at a sixth location on the bottom wall and operable to receive the optical signals from the first optical transmitter array and the second optical transmitter array, the fourth optical receiver spaced apart from the second optical receiver with the first optical transmitter array and the second optical transmitter array positioned therebetween.

7. The electronic fitness device of claim 6, wherein the third optical receiver and the fourth optical receiver each have an elongated aspect ratio, and wherein the third optical receiver is oriented longitudinally along the first axis and the fourth optical receiver is oriented along the second axis on the bottom wall.

8. The electronic fitness device of claim 6, further comprising:
a first lens covering the first optical transmitter array and configured to direct optical signals to the skin of the user,
a second lens covering the second optical transmitter array and configured to direct optical signals to the skin of the user, and
third, fourth, fifth, and sixth lenses, each lens covering a corresponding optical receiver and configured to direct optical signals exiting from the skin onto the associated optical receiver.

9. The electronic fitness device of claim 5, further comprising a third optical transmitter array positioned at a fifth location on the bottom wall approximately midway between the first optical transmitter array and the second optical transmitter array along the first axis and along the second axis, and operable to output a plurality of optical signals that pass through the user's skin, each optical signal having a wavelength equal to a wavelength of a corresponding optical signal of the first optical transmitter array.

10. An electronic fitness device comprising:
a housing including a bottom wall configured to contact a user's wrist;
a first optical transmitter array positioned at a first location on the bottom wall and including a first optical transmitter, a second optical transmitter, and a third optical transmitter, each optical transmitter operable to output a first optical signal that passes through a user's skin, each first optical signal having a unique wavelength;
a second optical transmitter array positioned at a second location on the bottom wall and including a first optical transmitter, a second optical transmitter, and a third optical transmitter, each optical transmitter operable to output a second optical signal that passes through a user's skin, each second optical signal having a wavelength equal to a wavelength of a corresponding first optical signal of the first optical transmitter array; and
a first optical receiver, a second optical receiver, a third optical receiver, and a fourth optical receiver,
the first optical receiver spaced apart from the third optical receiver with the first optical transmitter array and the second optical transmitter array positioned therebetween,
the second optical receiver spaced apart from the fourth optical receiver with the first optical transmitter array and the second optical transmitter array positioned therebetween, and
each optical receiver operable to receive the first optical signals and the second optical signals;
wherein the first optical signals travel along a different signal path from the first optical transmitter array to each of the optical receivers;
wherein the second optical signals travel along a different signal path from the second optical transmitter array to each of the optical receivers; and
wherein the first optical receiver is spaced apart from the first optical transmitter array along a first axis, and the second optical receiver is spaced apart from the first optical transmitter array along a second axis, the second axis orthogonal to the first axis, on the bottom wall.

11. The electronic fitness device of claim 10, wherein the first optical transmitter array and the second optical transmitter array are spaced apart from one another along the first axis and along the second axis on the bottom wall, and wherein each optical receiver is operable to generate a first electronic signal corresponding to the first optical signals and a second electronic signal corresponding to the second optical signals.

12. The electronic fitness device of claim 10, wherein the first optical receiver, the second optical receiver, the third optical receiver, and the fourth optical receiver each have an elongated aspect ratio, and wherein the first optical receiver and the third optical receiver are oriented longitudinally along a first axis, and wherein the second optical receiver and the fourth optical receiver are oriented along a second axis, orthogonal to the first axis, on the bottom wall.

13. The electronic fitness device of claim 10, further comprising:
a first lens covering the first optical transmitter array and configured to direct optical signals to the skin of the user,
a second lens covering the second optical transmitter array and configured to direct optical signals to the skin of the user, and
third, fourth, fifth, and sixth lenses, each lens covering a corresponding optical receiver and configured to direct optical signals exiting from the skin onto the associated optical receiver.

14. An electronic fitness device comprising:
a housing including a bottom wall configured to contact a user's wrist;
a memory element configured to store a signal to noise ratio threshold;
a first optical transmitter array positioned at a first location on the bottom wall and operable to output a plurality of first optical signals that pass through a user's skin, each first optical signal having a unique wavelength;
a second optical transmitter array positioned at a second location on the bottom wall and operable to output a plurality of second optical signals that pass through the user's skin, each second optical signal having a wavelength equal to a wavelength of a corresponding first optical signal;
a first optical receiver, a second optical receiver, a third optical receiver, and a fourth optical receiver, each optical receiver:
positioned on the bottom wall,
operable to receive the first optical signals and the second optical signals, and operable to generate a first electronic signal corresponding to the first optical signals and a second electronic signal corresponding to the second optical signals; and a processing element coupled with the memory element and each of the optical receivers, the processing element configured to:
receive the first electronic signal and the second electronic signal from each of the optical receivers,
determine a signal to noise ratio of each of the first electronic signals and the second electronic signals, and
process the first electronic signals and the second electronic signals if the signal to noise ratio of the first electronic signals and the second electronic signals is above the signal to noise threshold;
wherein the first optical receiver and the third optical receiver are spaced apart from the first optical transmitter array along a first axis, and the second optical receiver and the fourth optical receiver are spaced apart from the first optical transmitter array along a second axis, orthogonal to the first axis, on the bottom wall.

15. The electronic fitness device of claim 14, wherein the first optical transmitter array and the second optical transmitter array are spaced apart from one another along the first axis and along the second axis on the bottom wall.

16. The electronic fitness device of claim 14, wherein the first optical receiver is spaced apart from the third optical receiver with the first optical transmitter array and the second optical transmitter array positioned therebetween.

17. The electronic fitness device of claim 14, wherein the second optical receiver is spaced apart from the fourth optical receiver with the first optical transmitter array and the second optical transmitter array positioned therebetween.

18. The electronic fitness device of claim 14, wherein the first optical receiver, the second optical receiver, the third optical receiver, and the fourth optical receiver each have an elongated aspect ratio, and wherein the first optical receiver and the third optical receiver are oriented longitudinally along the first axis, and wherein the second optical receiver and the fourth optical receiver are oriented along the second axis on the bottom wall.

19. The electronic fitness device of claim 14, further comprising:
a first lens covering the first optical transmitter array and configured to direct optical signals to the skin of the user,
a second lens covering the second optical transmitter array and configured to direct optical signals to the skin of the user, and
third, fourth, fifth, and sixth lenses, each lens covering a corresponding optical receiver and configured to direct optical signals exiting from the skin onto the associated optical receiver.

20. The electronic fitness device of claim 14, further comprising
a third optical transmitter array positioned at a third location on the bottom wall approximately midway between the first optical transmitter array and the second optical transmitter array along the first axis and along the second axis, and operable to output a plurality of optical signals that pass through the user's skin, each optical signal having a wavelength equal to a wavelength of a corresponding optical signal of the first optical transmitter array; and
a fifth optical receiver, a sixth optical receiver, a seventh optical receiver, and an eighth optical receiver, each optical receiver operable to receive the first optical signals and the second optical signals and to generate the first electronic signal and the second electronic signal,
wherein the eight optical receivers are positioned along a circumference of a circular formation at angular intervals of approximately 45 degrees, such that the optical receivers surround the optical transmitter arrays.

* * * * *